(12) United States Patent
Stäbler

(10) Patent No.: US 6,452,010 B1
(45) Date of Patent: Sep. 17, 2002

(54) PROCESS FOR THE PREPARATION OF HYDROXAMIC ACID DERIVATIVES

(75) Inventor: Florian Stäbler, Weil am Rhein (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/566,707

(22) Filed: May 9, 2000

(30) Foreign Application Priority Data

May 11, 1999 (EP) .............................. 99109431

(51) Int. Cl.[7] .............................. C07D 211/14
(52) U.S. Cl. ................. 546/210; 548/319.1; 560/122
(58) Field of Search ............... 546/210; 548/319.1; 560/122

(56) References Cited

U.S. PATENT DOCUMENTS

| | | | |
|---|---|---|---|
| 2,483,252 A | 9/1949 | Tryon et al. | 554/94 |
| 4,837,362 A | 6/1989 | Fuchs et al. | 562/606 |
| 5,614,625 A | * 3/1997 | Broadhurst et al. | 540/480 |
| 5,932,759 A | * 8/1999 | Motoyama et al. | 560/160 |
| 5,952,507 A | 9/1999 | Hilpert | 546/226 |
| 6,031,103 A | 2/2000 | Brown et al. | 546/210 |

FOREIGN PATENT DOCUMENTS

| | | |
|---|---|---|
| EP | 0 108 294 | 5/1984 |
| EP | 3601216 | 1/1986 |
| EP | 3601216 | 7/1987 |
| EP | 0 684 240 | 11/1995 |
| EP | 0 816 341 | 1/1998 |
| EP | 0 818 442 | 1/1998 |
| EP | 0 911 324 | 4/1999 |
| EP | 0 974 590 | 1/2000 |
| WO | WO 96/00214 | 1/1996 |

OTHER PUBLICATIONS

Isomura et al. "Preparation of amide derivatives as collagenase inhibitors" CA 117:212156 (1992).*
Kovacic et al. "Aromatic amination with hydroxylammonium salts . . . " J. AM. Chem. Soc. v.84, 759–763 (1962).*

* cited by examiner

Primary Examiner—Ceila Chang
(74) Attorney, Agent, or Firm—George W. Johnston; Dennis P. Tramaloni

(57) ABSTRACT

The present invention provides an improved process for preparing an hydroxycarbamoyl derivative of a carboxylic acid using a hydroxylammonium salt of a carboxylic acid as a reagent.

7 Claims, No Drawings

PROCESS FOR THE PREPARATION OF HYDROXAMIC ACID DERIVATIVES

BACKGROUND OF THE INVENTION

The present invention relates to an improved process for the preparation of a hydroxamic acid derivative from the corresponding carboxylic acid.

Hydroxamic acid derivatives of certain carboxylic acids have been recognized as inhibitors of matrix metalloproteinases (MMPs) which are a family of proteases (enzymes) involved in the degradation and remodeling of connective tissues. Excessive degradation of extracellular matrix by MMPs is implicated in the pathogenesis of many diseases, including rheumatoid arthritis, osteoarthritis, multiple sclerosis, bone resorptive diseases (such as osteoporosis), chronic obstructive pulmonary disease, restenosis, cerebral hemorrhaging associated with stroke, periodontal disease, aberrant angiogenesis, tumor invasion and metastasis, corneal and gastric ulceration, ulceration of skin, aneurysmal disease, and in complications of diabetes. MMP inhibition is, therefore, recognized as a good target for therapeutic intervention of this type of diseases.

Current synthetic methods of introducing the hydroxylamine group in carboxylic acids and in particular such MMP inhibitors employ the reaction with a hydroxylammonium salt derived from an inorganic acid such as HCl, $H_2SO_4$ or $H_3PO_4$ etc. such as hydroxylammonium chloride, hydroxylammonium sulfate or hydroxylammonium phosphate (see e.g. EP 0 818 442 A2 or WO 96/00214 for such inhibitors and methods for making them, especially with regard to the introduction of the hydroxylamine group). However, these reagents have also drawbacks regarding side reactions, especially with sterically hindered or sensitive carboxylic acids, which reduce the yield of the compound obtained.

To overcome these problems, the reaction is then performed by employing O-derivatized hydroxylamine reagents like benzylhydroxylammonium chloride, O-tetrahydropyranyl-hydroxylamine or O-trimethylsilyl-hydroxylamine. All these reagents are O-protected reagents which have to be prepared separately and which require subsequent deprotection to yield the free hydroxylamine group.

Accordingly, there is still a need for providing an improved process for the preparation of hydroxamic acid derivatives in general and for those suitable as enzyme inhibitors in particular. This problem has been solved by the present invention.

SUMMARY OF THE INVENTION

The present invention provides a process for the manufacture of a hydroxamic acid derivative from the corresponding carboxylic acid, characterized in that the carboxyl group is reacted with a hydroxylammonium salt of a carboxylic acid in a suitable solvent. The "corresponding carboxylic acid" means the carboxylic acid precursor which is converted into the hydroxamic acid derivative.

It has unexpectedly been found that the hydroxylamine group can also be introduced by using a hydroxylammonium salt of an organic acid as a reagent. These reagents can advantageously be used as effective reagents to make the hydroxamic acid from the corresponding carboxylic acid, especially when the corresponding carboxylic acid is sterically hindered or very sensitive to basic conditions. Preferably, the carboxylic acid used in the hydroxylammonium salt reagent is different from the corresponding carboxylic acid it is reacted with especially if the corresponding carboxylic acid is difficult to obtain compared to acids useful in the reagent.

DETAILED DESCRIPTION OF THE INVENTION

The following definitions are used in the description. "Halogen" is to be understood hereinafter as chlorine, bromine and iodine. "Alkyl" signifies a straight-chain or branched alkyl group with 1 to 8C atoms, preferably 1–6C atoms, such e.g. methyl, ethyl, propyl, butyl, pentyl, hexyl, isopropyl and tert.butyl. "Alkoxy" means an Alkyl-O—group wherein one hydrogen has been replaced by an oxygen atom. "Aryl", alone or in combination, means a monovalent monocyclic or bicyclic aromatic hydrocarbon radical of 6 to 10 ring atoms e.g., phenyl, 1-naphthyl, 2-naphthyl, and the like. "Cycloalkyl", alone or in combination, means a saturated monocyclic ring of 3 to 7 carbon atoms, e.g., cyclopentyl, cyclohexyl or cycloheptyl.

In accordance with the present invention, a hydroxamic acid derivative is produced by reacting a carboxylic acid corresponding to the hydroxamic acid with an hydroxylammonium salt of an organic acid. The carboxylic acid corresponding to the hydroxamic acid derivative having the formula R—COOH, wherein R is any organic residue which when taken together with a carboxyl group forms an organic acid, is reacted with a hydroxylammonium salt of an organic acid having the formula $NH_2OH.HA$, wherein HA is an organic acid which is preferably different from the carboxylic acid corresponding to the hydroxamic acid derivative, to produce a hydroxamic acid derivative having the formula

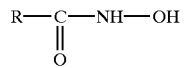

Preferably, the R group of the carboxylic acid corresponding to the hydroxamic acid does not contain a reactive group.

In the hydroxylammonium salt of the organic acid, i.e., the hydroxylammonium carboxylate, the anion is derived from an organic carboxylic acid of the general formula $R^4$—C(O)OH. $R^4$ can be any organic residue such as alkyl, cycloalkyl or an aryl and the like which residues (except H) can optionally be further substituted by halogen, nitro, carboxy and the like. Accordingly, dicarboxylic acids like oxalic acid, malonic acid, succinic acid, maleic acid or phthalic acid may be used as well. Monocarboxylic acids are preferred. Preferred carboxylic acid salts are hydroxylammonium acetate, hydroxylammonium propionate, hydroxylammonium benzoate and the like. Such salts have a higher solubility in organic solvents and, therefore, a better reactivity than the inorganic acid salts. Moreover, the carboxylate is a weak base which, based upon its reaction with the free protons in the reaction mixture, provides better reactivity of the non-protonized reagents and causes less side reactions. Most preferably, hydroxylammonium acetate is used.

The hydroxylammonium carboxylates can be prepared by treating a 50% solution of hydroxylamine in water with a carboxylic acid corresponding to the hydroxylamine in an alcohol such as methanol, ethanol or propanol at temperatures from –10 to 30° C. After cooling to temperatures below –10° C. the salt can be crystallized and subsequently washed and dried. Alternatively, DE 3601216 A1 also discloses a process for the preparation of hydroxylammonium salts of fatty acids with 1 to 4 carbon atoms, especially the acetate and the propionate, by reacting hydroxylammonium sulfate and alkali fatty acid salts in a suitable solvent. The preparation of organic acid salts has also been described in U.S. Pat. No. 2,483,252 and in EP 0 108 294 A2 where the oxalate, acetate, benzoate and formate salts are described.

For the introduction of the hydroxylamine group into the carboxylic acid R—COOH the carboxyl group is preferably activated. Any conventional method for activating the carboxyl group can be utilized. For example, this can be effected with activating agents known per se, such as carbodiimides, e.g. dicyclohexylcarbodiimide, or an isocyanide, e.g. tert-butyl isocyanide or, preferably, 2-morpholino-ethyl isocyanide in the presence of stoichiometric amounts of active ester-forming alcohols, such as e.g. N-hydroxy-succinimide, N-hydroxybenzotriazole or preferably N-hydroxy-2-pyridone, in a solvent, such as an ether, e.g. tert-butyl methyl ether, tetrahydrofuran or dioxane, or a hydrocarbon, e.g. toluene, or a halogenated hydrocarbon, e.g. $CH_2Cl_2$, $CCl_4$, preferably methylene chloride, or a nitrile, e.g. $CH_3CN$, or an ester, e.g. methyl- or ethyl acetate, preferably ethyl acetate, or an alcohol, e.g. methanol or ethanol, at a temperature of 0 to 80°, preferably 10 to 25°.

The temperature and pressure under which the reaction is carried out are not critical. The reaction can be performed at room temperature and atmospheric pressure. The reaction can optionally be performed with the addition of a base in order to neutralize the acid generated from the hydroxylammonium salt. In a preferred embodiment a base is added. Such an organic base may be an amine, preferably a tertiary amine, e.g. triethylamine or N-methylmorpholine.

Work up of the reaction mixture can be performed in the usual manner by extracting and washing the organic layer with water and/or aqueous buffers to eliminate the reagents. Further purification may be performed by chromatography and/or crystallization to obtain the final hydroxycarbamoyl derivative. The derivative may be crystallized in form of the free hydroxamic acid or as a salt using a suitable base. Alternatively, when the hydroxamic acid derivative is further substituted with a basic moiety, acid addition salts may be formed or, when the derivative is substituted with an acidic moiety, base addition salts may be formed by known methods.

In a particular embodiment of the process of the present invention 1-[3-cyclopentyl-2(R)-[1(R)-(hydroxycarbamoyl)-2-(3,4,4-trimethyl-2,5-dioxo-1-imidazolidinyl)ethyl]propionyl]piperidine (I)

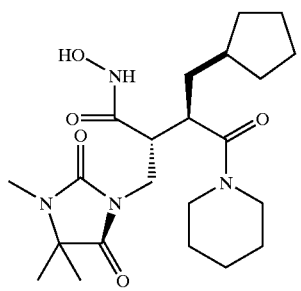

(I)

is prepared. This process comprises reacting a carboxylic acid compound of formula II

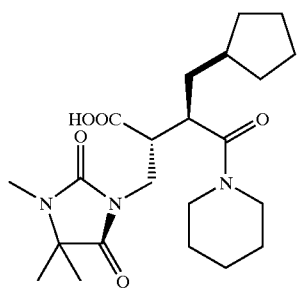

(II)

with a hydroxylammonium salt of an organic acid in a suitable solvent as described above. The compound of formula (II) is the preferred "corresponding carboxylic acid" referred to in the various embodiments of the process of the present invention as described herein.

Compound (I) is known and described, for example, in EP 684 240 A1. The compound has valuable pharmacological properties and can accordingly be used for the treatment of and presentation of illnesses such as, for example, degenerative joint diseases. The compound can be prepared as described in EP 0 684 240 A1 or as described in EP 0 816 341 A1.

Compound (I) can be prepared from the acid according to the description of the reaction conditions given above. In this connection, the organic acid or carboxylic acid used in the hydroxylammonium salt reagent has to be different from the carboxylic acid precursor with which it is reacted. Use of the hydroxylammonium salt of the sterically hindered carboxylic acid of formula II in the process of the present invention is not desirable because it would react unspecifically upon activation with both the oxygen and the nitrogen active center of hydroxylamine. Most preferably, hydroxylammonium acetate is used which unexpectedly provides the smallest amount of dimers of compounds of formula (II) bridged via the hydroxylamino group. Regarding the other reaction conditions the reaction is preferably performed in a solvent wherein the solvent is any conventional inert organic solvent, preferably a halogenated hydrocarbon, preferably $CH_2Cl_2$, or a nitrile, preferably $CH_3CN$, using hydroxylammonium acetate. The activated ester is preferably made with N-hydroxy-2-pyridone as the alcohol component. 2-morpholino-ethyl isocyanide is the preferred activator. Work up of the reaction mixture is done by washing the organic layer with water or an aqueous buffer. Further purification may be performed by subsequent chromatography on silica gel using $CH_2Cl_2$/MeOH. Alternatively, crystallization can be done in an organic solvent such as wet tert butyl methyl ether, or in water to obtain compound (I). Preferably, an organic acid, especially acetic acid, is added before concentrating the final organic layer, e.g. for crystallization, in particular if large scale synthesis of compound (I) is performed.

In connection with the manufacture of the compound of formula (I) via compound (II), compound (II) can be prepared as described in EP 0 684 240 A1 or as described in EP EP 0 816 341 A1. Moreover, compound (II) can be prepared by a) reacting a compound of formula (III)

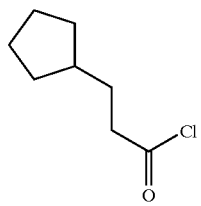

(III)

with (S)-4-benzyl-2-oxazolidone to give (S)-3-(3-cyclopentyl-1-oxopropyl)-4-(phenyl)-2-oxazolidinone (IV), b) the product obtained is reacted with a compound of formula (V)

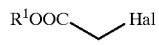

(V)

wherein $R^1$ signifies ($C_1$–$C_6$)alkyl or benzyl and Hal signifies chlorine, bromine or iodine, to give a compound of formula (VI)

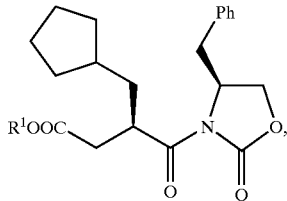

(VI)

c) cleaving of (S)-4-benzyl-2-oxazolidinone to obtain a compound of formula (VII)

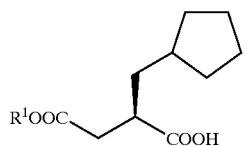

(VII)

d) reacting a compound of formula (VII) with piperidine to obtain a compound of formula (VIII)

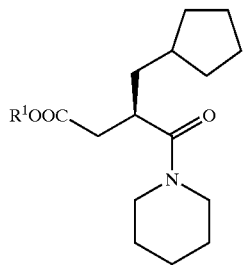

(VIII)

e) the thus-obtained compound of formula (VIII) is reacted with a halo-hydantoin of formula (IX)

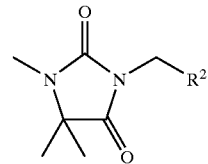

(IX)

wherein —$R^2$ is chlorine, bromine or iodine, in the presence of a strong, enolate-forming base, to give a compound of formula (X)

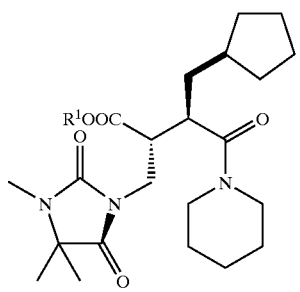

(X)

wherein $R^1$ signifies (C1–C6)alkyl or benzyl, and f) obtaining a compound of formula (II)

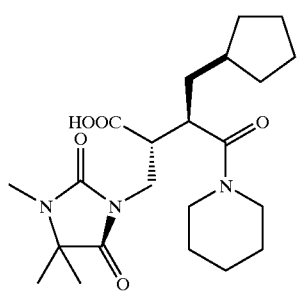

(II)

by cleaving of the $R^1$ group.

Compound (II) is then further reacted with an hydroxylammonium salt as described above to yield compound (I).

The acylation of (S)-4-benzyl-2-oxazolidinone (commercially available or producible according to M. Sudharshan, P. G. Hultin, Synlett, 171 (1997)) with cyclopentyl-propionyl chloride (III) (Barret et al., J. Chemical Society 1065 (1935)) in accordance with step a) is effected according to methods known per se with a base, e.g. NaH, LDA, LiN(TMS)$_2$, or an alkyllithium compound, preferably BuLi, in a solvent such as an ether, preferably THF, at a temperature of −80° to 22°, preferably −45°. For the formation of the alkylated compounds (VI) in step b), the (S)-3-(3-cyclopentyl-1-oxopropyl)-4-(phenylmethyl)-2-oxazolidinone which remains can be used in isolated form or, conveniently, in solution. The alkylation is effected with a halo-acetic acid ester, preferably tert-butyl bromoacetate in the presence of a base, e.g. LiN(TMS)$_2$ or preferably LDA in an aforementioned solvent, preferably THF, at −80° to 22°, preferably −45°. The product (VI) which is formed can be obtained from the reaction medium in high optical purity (de>99.9%) by crystallization following the addition of an alkane, preferably hexane, or by chromatography.

The halo-acetic acid esters are commercially available or obtainable according to methods per se by the esterification of haloacetic acid derivatives.

The cleavage of the chiral auxiliary reagent from compounds of formula (VI) to give the acid (VII) and (S)-4-benzyl-2-oxazolidinone in accordance with step c) can be effected according to methods known per se with hydrogen peroxide and LiOH in an ether, such as e.g. tetrahydrofuran. Alternatively, the reaction also proceeds quantitatively when sodium hydroxide and hydrogen peroxide in a mixture of water and an alcohol, preferably isopropanol, is used at a temperature of −10° to 22°, preferably 0°. The (S-)-4-benzyl-2-oxazolidinone, which is thereby obtained, crystallizes out almost quantitatively from the aqueous phase.

The amide formation of the acid (VII) with piperidine in step d) can be effected according to coupling methods known per se, such as e.g. via the acid chloride, via a mixed anhydride, via a mixed sulphonic acid anhydride or, preferably, via an active ester. In so doing there are used water-withdrawing agents such as carbodiimides, preferably dicyclohexyl-carbodiimide in the presence of stoichiometric or catalytic amounts of active ester-forming alcohols, such as e.g. N-hydroxysuccinimide, N-hydroxybenzotriazole or preferably N-hydroxy-2-pyridone in a solvent such as a ketone, e.g. methyl ethyl ketone, or an ether, e.g. tert-butyl methyl ether, or a hydrocarbon, e.g. toluene, or a halogenated hydrocarbon, e.g. methylene chloride, or an ester, preferably isopropyl acetate, at a temperature of 0 to 80°, preferably 22°.

The alkylation of compounds of formula VIII with the halomethyl-hydantoin (IX) in step e) is effected in a presence of a strong base in a solvent such as an ether, preferably THF, at a temperature of −100° to 22°, preferably −60° C. With strong, enolate-forming potassium bases, such as e.g. $KN(TMS)_2$ or C1–C6-alkoxy potassium bases, such as e.g. potassium tert.-butylate, KH, or $KNH_2$ the anti-selectivity required for the manufacture of compounds of formula (X) is achieved. The mixture of diastereomers can be separated by chromatography on silica gel with suitable solvents, such as, for example, hexane/ethyl acetate.

The halohydantoin (IX) used for the reaction with a compound (VIII) can be obtained by halomethylation of 1,5,5-trimethyl-hydantoin. Thus, 1,5,5-trimethyl-hydantoin is conveniently reacted with a hydrogen halide in acetic acid at a temperature between 20° and 100°, preferably at about 80°. The trimethyl-hydantoin can be obtained according to methods known per se (H. Heimgartner et al., Helv. Chim. Acta 75, 1251 (1992)).

The hydrolysis of an ester group in a compound of formula (X) in which $R^1$ signifies straight-chain or branched $(C_1–C_6)$alkyl, other than tert-butyl or a similar sterically hindered alkyl group, to the compound (II) in accordance with section f) is effected in the presence of an alkali or alkaline earth metal hydroxide, such as barium, calcium, sodium or potassium hydroxide, preferably potassium hydroxide, in a solvent such as an alcohol, e.g. i-propanol, or water with an organic solvent, such as an ether, e.g. tert-butyl methyl ether, or preferably THF, at a temperature of 0 to 100°, preferably 30 to 50°.

The cleavage of the tert-butyl group or a similar sterically hindered alkyl group like iso-propyl or sec-butyl, which are not easily accessible to base cleavage, in a compound of formula (X) to give the compound (II) in accordance with section f) is effected in the presence of a mineral acid, such as e.g. aqueous phosphoric or sulphuric acid, preferably hydrochloric acid or hydrobromic acid and an organic carboxylic acid, preferably acetic acid at a temperature of 0 to 100°, preferably 0–22°. The cleavage can also be carried out in a carboxylic acid ester or a mixture of carboxylic acid and carboxylic acid ester in place of a carboxylic acid. Suitable carboxylic acid esters are methyl, ethyl or isopropyl acetate, preferably ethyl acetate. Preferably, the cleavage in section f) is effected with a mineral acid in a carboxylic acid, preferably with HBr/acetic acid. Furthermore, the cleavage by means of an acid can be effected in an otherwise suitable organic solvent. Methylene chloride or toluene is a suitable organic solvent.

The debenzylation of the compound (X) in which $R^1$ is equal to benzyl (Bz) in section e) to give compound (II) is effected in an organic solvent using hydrogen in the presence of a metal catalyst. Suitable solvents are $C_1–C_6$-alcohols, preferably methanol or ethanol. As metal catalysts there can be used platinum or palladium, which are conveniently supported on a carrier material such as aluminium oxide, barium sulphate or charcoal. Palladium on charcoal or barium sulphate is a preferred catalyst. Temperature and pressure are not critical and can be varied in a wide range. Preferably, the hydrogenation is carried out at room temperature and 1–10 bar.

The invention is now further described by way of examples which are not intended to be limiting the scope of the claims.

EXAMPLES

In the Examples and the description the following abbreviations have been used:

ee enantiomeric excess

GC gas chromatography (on fused silica) for determining the amount of product obtained hr(s) hour(s)

MS (ISP, EI) Mass Spectroscopy (ISP: Ion Spray positive; EI: Electron Ionization)

r.t. room temperature m.p. melting point

All temperatures are given in degree Celsius.

Example 1

Preparation of Hydroxylammonium Acetate Salt 100 g hydroxylamine solution (50% in water) was placed in a 500 ml flask and cooled in ice bath (0–5°) with a magnetic stirrer. 93 g glacialic acid were added slowly with stirring over 30 min and cooling. The mixture was cooled to −20° C. and the suspension was filtered. The crystals were washed with tert-butylmethyl ether and dried in vacuum on the rotavap at 35° C. yielding 131 g (91%) white crystals of hydroxylammonium acetate. m.p. 87°.

Example 2

30 g 1-[2(R)-[1(R)-carboxy-2-(3,4,4,-trimethyl-2,5-dioxo-1-imidazolidinyl)-ethyl]-3-cyclopentylpropionyl] piperidine and 8.71 g N-hydroxy-pyridone were dissolved in 120 ml $CH_2Cl_2$ in a 250 ml round bottom flask. The mixture was treated at r.t. with 10.73 g morpholinoethylisocyanide. After 10–20 min the mixture turned clear and stirring was continued at r.t. overnight. The solution was slowly added to a stirred suspension of 9.94 g hydroxylammonium acetate and 7.2 g triethylamine in 180 ml $CH_2Cl_2$ and the mixture was stirred for an additional 4 h. The reaction mixture contains about 97% product and about 3% starting material. This mixture was extracted with 95 ml water. The aqueous layer was extracted with 60 ml $CH_2Cl_2$ and the combined organic layers extracted twice with 95 ml (total 190 ml) 5%

NaHCO₃ solution and once with 95 ml 2% H₂SO₄ solution. The organic layer was evaporated at 35–40°. The oily residue was treated with 300 ml wet tert butyl methyl ether and evaporated to a volume of 200 ml and stirred for 10 hrs. The solid was filtered off, washed twice with 20 ml tert butyl methyl ether and dried under reduced pressure at r.t. yielding 25.6 g (82%) of pure 1-[3-cyclopentyl-2(R)-[1(R)-(hydroxycarbamoyl)-2-(3,4,4-trimethyl-2,5-dioxo-1-imidazolidinyl)ethyl]propionyl]piperidine MS (EI): 436, m.p. 120° dec.

Example 3 a) According to the procedure described in Example 2 but by reacting 10 g of 1-[2(R)-[1(R)-carboxy-2-(3,4,4,-trimethyl-2,5-dioxo-1-imidazolidinyl)-ethyl]-3-cyclopentylpropionyl]piperidine with 2.9 g N-hydroxypyridone and 3.66 g morpholinoethyl isocyanide and subsequent reaction with 2.47 g hydroxylammonium chloride and 6 g triethylamine 50% of the dimer were obtained. This dimer further reacted to the product and starting material. The final reaction mixture contained 55% product, 25% starting material and 18% dimer.

b) Reacting 1-[2(R)-[1(R)-carboxy-2-(3,4,4,-trimethyl-2,5-dioxo-1-imidazolidinyl)-ethyl]-3-cyclopentylpropionyl]piperidine with hydroxylammonium sulfate in an analogous manner as described in a) the same reaction mixture composition was obtained.

c) Reacting 1-[2(R)-[1(R)-carboxy-2-(3,4,4,-trimethyl-2,5-dioxo-1-imidazolidinyl)-ethyl]-3-cyclopentylpropionyl]piperidine with hydroxylammonium phosphate gave the same rection mixture as in a).

d) According to the procedure described in a) but by reacting 2.5 g of 1-[2(R)-[1(R)-carboxy-2-(3,4,4,-trimethyl-2,5-dioxo-1-imidazolidinyl)-ethyl]-3-cyclopentylpropionyl]piperidine with 0.73 g N-hydroxypyridone and 0.92 g of morpholinoethyl isocyanide and subsequent reaction with 0.94 g hydroxylamine (50% in water) dissolved in methanol (2.25 ml) and water (0.3 ml) gave a reaction mixture containing 80% product and 16% of the corresponding aminoester (reaction at the O-terminal of hydroxylamine).

Example 4

The starting material used in Example 2 was prepared in the following manner:

a) A solution of 53.1 g of (S)-4-benzyl-2-oxazolidinone in 420 ml of tetrahydro-furan was treated at −45° with 197 ml of 1.6M butyllithium in hexane, a solution of 49.18 g of cyclopentylpropionyl chloride in 105 ml of tetrahydrofuran was subsequently added and the solution was stirred at −45° for 1 hr. The (S)-3-(3-cyclopentyl-1-oxopropyl)-4-(phenylmethy)-2-oxazolidinone resulting as an intermediate was treated with 286 ml of a 1.1M lithium diisopropylamide solution in tetrahydrofuran at −45°, stirred for 1.5 hrs. and subsequently 64.38 g of tert-butyl bromoacetate in 60 ml of tetrahydrofuran were added. After 4 hrs. at −45° 600 ml of semi-saturated ammonium chloride solution were added, the THF phase was washed with semi-saturated sodium chloride solution, concentrated and crystallized by the addition of hexane, with 94.5 g (76%) of pure (de>99.9%) tert-butyl (R)-4-[(S)-4-benzyl-2-oxo-oxazolidin-3-yl]-3-cyclopentylmethyl-4-oxo-butanoate, m.p. 113–119°, being obtained. IR (KBr): 1768s, 1730s and 1695s (C=O).

b) A solution consisting of 36.7 g of 35% hydrogen peroxide and 8.31 g of sodium hydroxide in 78 ml of water was added at 0° to a suspension of 78.5 g of the oxazolidinone from a) in 550 ml of isopropanol and the mixture was stirred at 22° for 1 hr. The solution was concentrated, made basic with sodium hydroxide solution and the precipitated (S)-4-benzyl-2-oxazolidinone was filtered off. Still present (S)-4-benzyl-2-oxazolidinone was extracted with methylene chloride, whereafter a total of 32.68 g (98%) of pure (S)-4-benzyl-2-oxazolidinone, m.p. 86.5–88°, was recovered. The aqueous phase was adjusted to pH 3 with hydrochloric acid and extracted with isopropyl acetate. The organic extracts were washed, dried and evaporated, after which 47.79 g (99%) of enantiomerically pure (ee>99%) (R)-2-cyclopentyl-methyl-succinic acid 4-tert-butyl ester were obtained as an oil. IR (film): 2700m, br. (COOH), 1733s and 1710s (C=O).

c) A suspension of 34.48 g of the acid from b) and 5.98 g of N-hydroxy-2-pyridone in 170 ml of isopropyl acetate was treated at 0° with 12.03 g of piperidine and subsequently with a solution of 30.53 g of dicyclohexyl-carbodiimide in 92 ml of isopropyl acetate and stirred at 22° for 16 hrs. The suspension was treated with 82 g of 10% acetic acid in water and the mixture was stirred for 4 hrs. and filtered. The organic phase was washed with sodium carbonate and water, filtered and concentrated, after which 43.89 g (100%) of pure tert-butyl (R)-3-cyclopentylmethyl-4-oxo-4-piperidin-1-yl-butanoate (ee>99%), m.p. 38–40°, crystallizing from the oil, were obtained. IR (film): 1729s and 1641s (C=O).

d) A solution of 10.7 g of the ester from c) in 50 ml of tetrahydrofuran was added dropwise at −60° to a solution of 8.76 g of potassium bis-trimethylsilylamide in 80 ml of tetrahydrofuran and the mixture was stirred at −60° for 30 min. Subsequently, a solution of 7.76 g of 3-bromomethyl-1,5,5-trimethylhydantoin in 40 ml of tetrahydrofuran was added at −60° and the mixture was stirred at −60° for 30 min. The reaction mixture was washed with semi-saturated sodium chloride solution and with dilute hydrochloric acid, dried, filtered and concentrated, there being obtained 15.11 g of a 9:1 mixture of 1-[2(R)-[1(R)-(tert-butoxycarbonyl)-2-(3,4,4-trimethyl-2,5-dioxo-1-imidazolidinyl) ethyl]-3-cyclopentylpropionyl]piperidine and 1-[2(R)-[1(S)-(tert-butoxycarbonyl)-2-(3,4,4-trimethyl-2,5-dioxo-1-imidazolidinyl)ethyl]-3-cyclopentylpropionyl]-piperidine, which was used in the next step without further purification. The mixture can be separated by chromatography on silica gel with hexane/ethyl acetate (1:1).

e) A solution of 15.11 g of the 9:1 mixture from d) in 15 ml of acetic acid was treated at 0° with 15 ml of 33% hydrogen bromide in acetic acid and stirred at 0° for 4 hrs. The solution was diluted with methylene chloride, washed with water and the organic phase was dried, filtered and evaporated. The residue was crystallized from 26 ml of tert-butyl methyl ether and 26 ml of hexane, after which 6.90 g (70%) of diastereomer-pure (de>98%) 1-[2(R)-[1(R)-carboxy-2-(3,4,4-trimethyl-2,5-dioxo-1-imidazolidinyl)ethyl]-3-cyclopentylpropionyl]piperidine, m.p. 111–114°, was obtained. IR (KBr): 1770m and 1715s (C=O).

What is claimed is:

1. A process for the manufacture of a hydroxamic acid derivative comprising reacting a carboxylic acid is 1-[2(R)-[1(R)carboxy-2-(3,4,4-trimethyl-2,5-dioxo-1-imidazolidinyl)-ethyl]-3-cyclopentylpropionyl]piperidine with an hydroxylammonium salt of an organic acid having the formula

NH₂OH.HA wherein HA is an organic acid which is different from the carboxylic acid;

in the presence of a solvent to produce the hydroxamic acid derivative having the formula

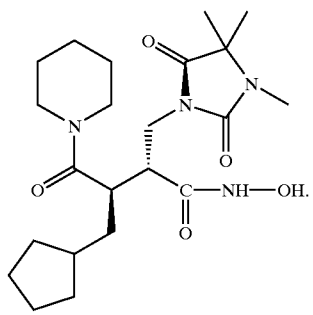

2. A process for the manufacture of 1-[3-cyclopentyl-2 (R)-[1(R)-(hydroxycarbamoyl)-2-(3,4,4-trimethyl-2,5-dioxo-1-imidazolidinyl)ethyl]propionyl]piperidine of formula (I)

(I)

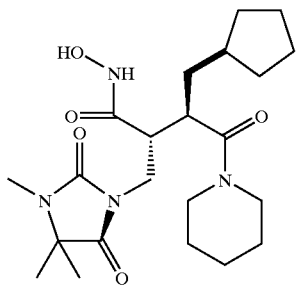

comprising reacting a carboxylic acid of formula (II)

(II)

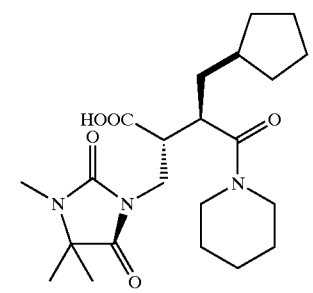

in the presence of a solvent with a hydroxylammonium salt of an organic acid having the formula $NH_2OH \cdot HA$ wherein HA is an organic acid which is different from the carboxylic acid of formula II to produce the compound of formula (I).

3. The process according to claim 2, wherein the hydroxylammonium salt is selected from the group consisting of hydroxylammonium acetate, hydroxylammonium propionate and hydroxylammonium benzoate.

4. The process according to claim 3, wherein the hydroxylammonium salt is hydroxylammonium acetate.

5. The process according to claim 2, wherein the reaction is carried out in the presence of a base.

6. The process according to claim 5, wherein the base is triethylamine.

7. The process according to claim 2, wherein the solvent is a halogenated hydrocarbon.

\* \* \* \* \*